(12) United States Patent
van den Honert et al.

(10) Patent No.: US 8,880,180 B2
(45) Date of Patent: Nov. 4, 2014

(54) ASSESSING NEURAL SURVIVAL (75) Inventors: Christoper van den Honert, Boulder, CO (US); Zachary Smith, Englewood, CO (US); Christopher J. Long, Centennial, CO (US); Robert P. Carlyon, Cambridge (GB)

(73) Assignee: Cochlear Limited, Macquarie University, NSW (AU)

(*) Notice: Subject to any disclaimer, the term of this patent is extended or adjusted under 35 U.S.C. 154(b) by 1391 days.

(21) Appl. No.: 12/172,821

(22) Filed: Jul. 14, 2008

(65) Prior Publication Data
US 2009/0132005 A1  May 21, 2009

Related U.S. Application Data

(60) Provisional application No. 60/949,682, filed on Jul. 13, 2007, provisional application No. 60/949,647, filed on Jul. 13, 2007.

(51) Int. Cl.
*A61N 1/00* (2006.01)
*A61B 5/12* (2006.01)
*A61B 5/00* (2006.01)
*A61N 1/36* (2006.01)

(52) U.S. Cl.
CPC .............. *A61B 5/121* (2013.01); *A61B 5/7217* (2013.01); *A61N 1/36032* (2013.01)
USPC ........................................................ 607/55

(58) Field of Classification Search
USPC ..................................... 607/55–57
See application file for complete search history.

(56) References Cited

U.S. PATENT DOCUMENTS

| 4,284,856 A | 8/1981 | Hochmair et al. |
| 4,357,497 A | 11/1982 | Hochmair et al. |
| 4,495,384 A | 1/1985 | Scott et al. |
| 4,535,785 A * | 8/1985 | van den Honert et al. ..... 600/559 |
| 4,947,844 A | 8/1990 | McDermott |
| 5,983,139 A | 11/1999 | Zierhofer |
| 6,074,422 A * | 6/2000 | Berrang et al. ................. 623/10 |
| 6,594,525 B1 | 7/2003 | Zierhofer et al. |

(Continued)

FOREIGN PATENT DOCUMENTS

| WO | 2009010870 | 1/2009 |
| WO | 2009013616 | 1/2009 |

OTHER PUBLICATIONS

Terry A. Zwolan, "Electrode discrimination and speech recognition in postlingually deafened adult cochlear implant subjects", J. Acoust. Soc. Am. 102(5), Dec. 1997 (13 pages).

(Continued)

*Primary Examiner* — Christopher D Koharski
*Assistant Examiner* — Roland Dinga
(74) *Attorney, Agent, or Firm* — K&L Gates LLP (57) ABSTRACT

Neural survival related to a cochlear implant may be assessed by determining stimulus efficacy for both focused and unfocused stimulation at a plurality of locations adjacent nerve tissue; and comparing stimulus efficacy for both the focused and unfocused stimulation at a plurality of locations to determine a measure of neural survival. In particular small differences in effects produced by unfocused and focused stimulation at each of the locations tends to indicate good survival at those locations and conversely large differences in effects of focused and unfocused stimulation at a given location indicate poor survival at that location.

17 Claims, 6 Drawing Sheets

(56) References Cited

U.S. PATENT DOCUMENTS

| | | | |
|---|---|---|---|
| 6,600,955 | B1 | 7/2003 | Zierhofer et al. |
| 6,751,505 | B1 | 6/2004 | Van Den Honert et al. |
| 6,915,166 | B1 | 7/2005 | Stecker et al. |
| 7,043,303 | B1 * | 5/2006 | Overstreet ............... 607/57 |
| 7,103,417 | B1 | 9/2006 | Segel et al. |
| 7,110,821 | B1 | 9/2006 | Ross |
| 7,136,706 | B1 | 11/2006 | Voelkel |
| 7,149,583 | B1 * | 12/2006 | Litvak ..................... 607/57 |
| 7,174,215 | B2 | 2/2007 | Bradley |
| 7,206,640 | B1 | 4/2007 | Overstreet |
| 7,209,789 | B2 | 4/2007 | Zierhofer et al. |
| 7,231,257 | B2 | 6/2007 | McDermott et al. |
| 7,283,876 | B2 | 10/2007 | Zierhofer et al. |
| 7,292,891 | B2 | 11/2007 | Hartley et al. |
| 2003/0163060 | A1 * | 8/2003 | Maddess et al. ............ 600/544 |
| 2006/0052841 | A1 | 3/2006 | Daly et al. |
| 2006/0247735 | A1 * | 11/2006 | Honert ..................... 607/57 |
| 2006/0265061 | A1 | 11/2006 | Kwon et al. |
| 2007/0129771 | A1 * | 6/2007 | Kurtz et al. ............... 607/48 |
| 2009/0132006 | A1 | 5/2009 | van den Honert et al. |

OTHER PUBLICATIONS

Bryan E. Pfingst et al., "Across-Site Variation in Detection Thresholds and Maximum Comfortable Loudness Levels for Cochlear Implants", JARO 5: 11-24 (2004) (14 pages).

Paul J. Abbas et al., "Summary of Results Using the Nucleus CI24M Implant to Record the Electrically Evoked Compound Action Potential", Ear and Hearing, vol. 20, No. 1, pp. 45-59, Feb. 1999 (15 pages).

Monita Chatterjee et al., "Effects of Stimulation Mode, Level and Location on Forward-Masked Excitation Patterns in Cochlear Implant Patients", JARO 7: 15-25 (2006) (11 pages).

Extended European Search Report for European Application No. 08789109.9 dated Feb. 7, 2012 (12 pages).

Extended European Search Report for European Application No. 08826588.9 dated Feb. 9, 2012 (11 pages).

International Searching Authority, "International Search Report," issued in connection with International Patent Application No. PCT/IB2008/002177, mailed on Aug. 31, 2009 (3 pages).

International Searching Authority, "Written Opinion," issued in connection with International Patent Application No. PCT/IB2008/002177, mailed on Aug. 31, 2009 (6 pages).

The International Bureau of WIPO, "International Preliminary Report on Patentability," issued in connection with International Patent Application No. PCT/IB2008/002177, on Jan. 19, 2010 (7 pages).

International Searching Authority, "International Search Report," issued in connection with International Patent Application No. PCT/IB2008/002178, mailed on Jul. 24, 2009 (1 page).

International Searching Authority, "Written Opinion," issued in connection with International Patent Application No. PCT/IB2008/002178, mailed on Jul. 24, 2009 (4 pages).

The International Bureau of WIPO, "International Preliminary Report on Patentability," issued in connection with International Patent Application No. PCT/IB2008/002178, on Jan. 19, 2010 (5 pages).

Bierer et al., "Cortical Responses to Cochlear Implant Stimulation: Channel Interactions," published in pp. 32-48, vol. 5, No. 1, Journal of the Association for Research in Otolaryngology, Mar. 2004 (published online on Oct. 2003) (17 pages).

Bierer, Julie Arenberg, "Threshold and Channel Interaction in Cochlear Implant Users: Evaluation of the Tripolar Electrode Configuration," published in pp. 1642-1653, vol. 121, No. 3, The Journal of the Acoustical Society of America, Mar. 2007 (12 pages).

Busby et al., "Pitch Perception for Different Modes of Stimulation Using the Cochlear Multiple-Electrode Prosthesis," published in pp. 2658-2669, Vo. 95, No. 1, The Journal of the Acoustical Society of America, May 1994 (12 pages).

Cohen et al., "Spatial Spread of Neural Excitation in Cochlear Implant Recipients: Comparison of Improved ECAP Method and Psychophysical Forward Masking," published in pp. 72-87, vol. 179, Hearing Research, May 2003 (16 pages).

Dingemanse et al., "Psychophysical Assessment of Spatial Spread of Excitation in Electrical Hearing with Single and Dual Electrode Contact Maskers," pp. 645-657, vol. 27, No. 6, Ear and Hearing, Dec. 2006 (13 pages).

Hall, Robert D., "Estimation of Surviving Spiral Ganglion Cells in the Deaf Rat Using the Electrically Evoked Auditory Brainstem Response," published in pp. 123-136, vol. 45, Hearing Research, 1990 (14 pages).

Hall, Robert D., "Estimation of Surviving Spiral Ganglion Cells in the Deaf Rat Using the Electrically Evoked Auditory Brainstem Response," published in pp. 155-168, vol. 49, Hearing Research, Nov. 1990 (14 pages).

Honert et al., "Focused Intracochlear Electric Stimulation with Phased Array Channels," published in pp. 3703-3716, vol. 121, No. 6, The Journal of the Acoustical Society of America, Jun. 2007 (14 pages).

Honert et al., "Single Fiber Mapping of Spatial Excitation Patterns in the Electrically Stimulated Auditory Nerve," published in pp. 195-206, vol. 29, Hearing Research, 1987 (12 pages).

Kwon et al., "Effect of Electrode Configuration on Psychophysical Forward Masking in Cochlear Implant Listeners," pp. 2994-3002, vol. 119, No. 5, The Journal of the Acoustical Society of America, May 2006 (9 pages).

* cited by examiner

ASSESSING NEURAL SURVIVAL

CROSS-REFERENCE TO RELATED APPLICATIONS

This application claims the benefit of U.S. Provisional Application No. 60/949,682, entitled "USE OF FOCUSED STIMULI TO MEASURE A NEURAL EXCITATION PROFILE WITHIN THE COCHLEA," filed Jul. 13, 2007 and U.S. Provisional Application No. 60/949,647 entitled "USE OF FOCUSED STIMULI TO MEASURE A NEURAL EXCITATION PROFILE WITHIN THE COCHLEA", filed Jul. 13, 2007. This application is related to U.S. Utility patent application entitled "USING INTERACTION TO MEASURE NEURAL EXCITATION" filed on Jul. 14, 2008 which is hereby incorporated by reference herein.

BACKGROUND

1. Field of the Invention

The present invent relates generally to assessing neural survival, and more particularly, to assessing neural survival associated with an implanted electrode array.

2. Related Art

Use of a cochlear implant (CI) has become an accepted therapy for treatment of severe or profound hearing impairment. As performance of these devices has increased over time the indications for use of the cochlear implant (CI) have been relaxed to allow treatment of individuals with greater degrees of residual hearing. This trend may be expected to continue in the future.

Hearing impairment may be caused by a variety of toxins, disease processes, and developmental failures. Most etiologies of deafness result in degeneration of some auditory neurons or their peripheral processes. In most cases there is a general trend toward greater neural degeneration in the base or high-frequency end of the cochlea, and less degeneration at progressively more apical places where lower frequencies are represented. However, there is very large variability across individuals in both the extent and spatial pattern of neural degeneration. Neural survival may be "patchy" and discontinuous.

Cochlear implants function by stimulating the surviving neurons. In order to optimize the operation of an implant for a specific individual recipient, it would be of value to know how neural survival varies across differing frequency places within the cochlea. However, no reliable method currently exists for assessing such neural survival patterns.

SUMMARY

In accordance with one aspect, the invention provides a method for assessing neural survival in a region encompassing a cochlear implant and adjacent nerve tissue, the method comprising: determining stimulus efficacy for both focused and unfocused stimulation at a plurality of locations adjacent the nerve tissue; and comparing stimulus efficacy for both the focused and unfocused stimulation at the plurality of locations to determine a measure of neural survival.

BRIEF DESCRIPTION OF THE DRAWINGS

The present invention will now be further described in the following portions of this application in conjunction with the attached drawings in which like reference characters identify identical apparatus and in which.

DETAILED DESCRIPTION

The invention allows collection of data and provides procedures which assess neural survival or local neural density. In order to estimate local neural density, aspects of the invention rely on an analysis of differences in stimulus efficacy between a focused stimulus and an unfocused stimulus. The effective intensity of an electric stimulus to a neuron depends upon the gradient of the potential field along the axis of the neural processes (central and/or peripheral). Focused and unfocused stimuli delivered at the same place have similar slope at the point of primary current injection. However the slope of the focused stimulus drops rapidly with distance from that point, whereas the slope of an unfocused stimulus drops more gradually. If many neurons lie near the primary point of current injection (i.e. within the region where the slopes are similar) focused and unfocused stimuli will have similar efficacy. However if few neurons fall within that region, the efficacy of the focused stimulus will be lower. The extent of the disparity in efficacy between focused and unfocused stimulation may be used to estimate the relative density of neurons near the primary point of current injection.

Stimulus efficacy may also be influenced by proximity of the electrode contacts to the modiolar wall. Some embodiments also analyze tissue impedance at the primary point of current injection (excluding series interface impedance of the metal-electrolyte boundary). High impedance indicates close proximity to the modiolus, whereas low impedance indicates greater distance. If stimulus efficacy is not correlated with high impedance, i.e., inferred contact proximity, then the neural density estimate described above is not adjusted. On the other hand if there is a nonnegligible correlation between inferred contact proximity (via indications of high impedance) and stimulus efficacy (focused or unfocused), the efficacy measure(s) may be corrected for proximity before the comparison is made.

In a preferred embodiment focused stimulation is implemented with phased array (PA) stimulation wherein many or all electrodes take part in the energization process. Alternatively, other techniques (employing fewer than all electrodes, with suboptimal weighting, etc.) may be used to provide focused stimulation albeit not as focused as that provided by the PA technology. Other alternatives for the focused stimulation include using a set of only three electrodes. Simple symmetric quadrupolar or tripolar stimuli may also provide sufficient focusing for a useful implementation.

The unfocused stimulus may use a group of multiple monopolar channels or bipolar channels.

Stimulus efficacy is preferably determined by determining a response threshold, i.e., determining where, in a schedule of increasing stimulus intensity, the threshold for a response is found. The response may be (preferably) perceptual so the threshold represents the lowest intensity at which a recipient becomes aware of the stimulus, or evoked, where the response represents the lowest intensity at which a response potential reaches some predetermined criterion. The comparison of stimulus efficacy is preferably implemented by determining a difference between thresholds for focused and unfocused stimulation. More extensive neural survival is indicated by small or minimal differences in the thresholds whereas greater differences in the thresholds indicate reduced neural survival.

As an alternative to the use of the perceptual threshold, minimum current to produce an evoked potential (e.g. auditory nerve compound action potential, or electrical auditory brainstem response) of specific magnitude may be used as a metric of stimulus efficacy. As an alternative to current at threshold (to elicit a percept or evoked potential) voltage in the fluid adjacent to the electrode contact may be compared for the focused and unfocused cases. As an alternative metric of stimulus efficacy the loudness or evoked potential magnitude at a specific current level may be employed.

Figure 1:
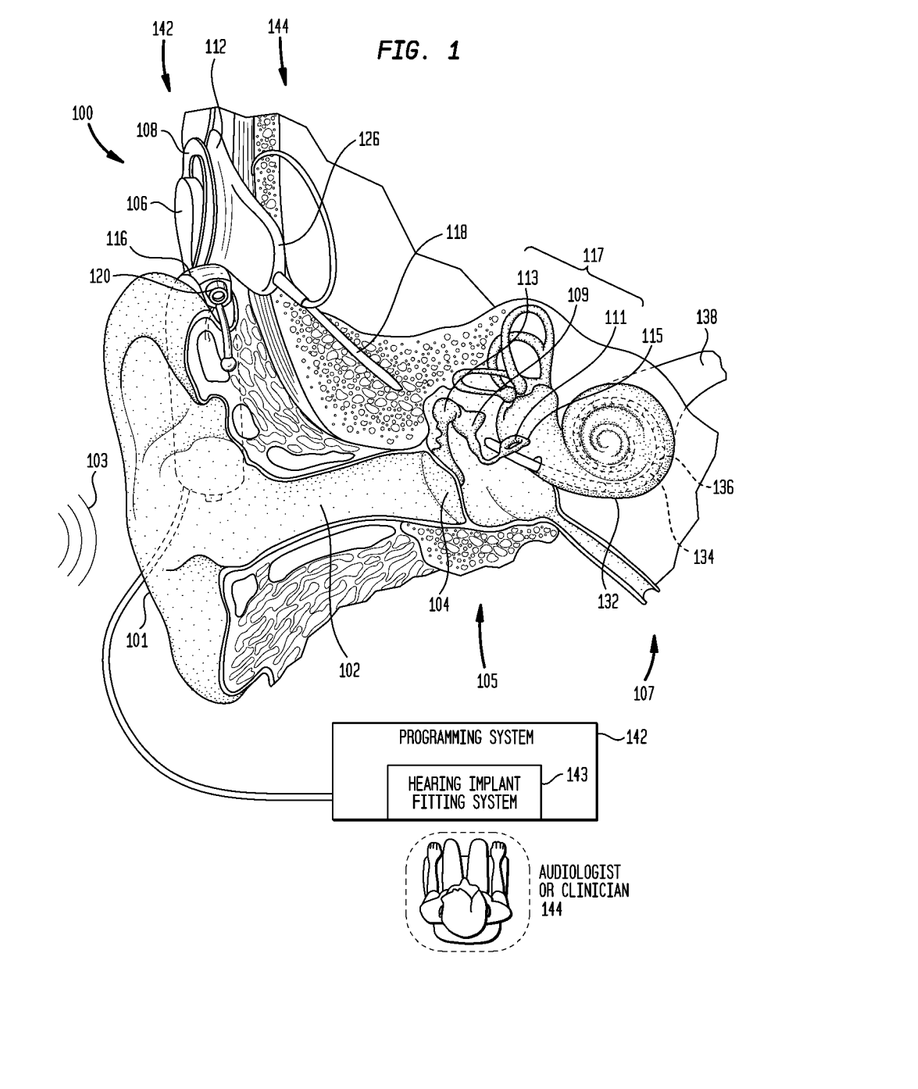
FIG. 1 schematically shows a conventional cochlear implant in place in a recipient's ear and associated apparatus including a programming system 142 available for operation by an audiologist or clinician.

FIG. 1 is a perspective view of an exemplary stimulating prosthetic hearing implant, comprising Cochlear implant 100. The present invention may be applied to glean important information about the characteristics of the implant as will be described. The relevant components of outer ear 101, middle ear 105 and inner ear 107 are described next below, followed by a description of Cochlear implant 100.

An acoustic pressure or sound wave 103 is collected by outer ear 101 (that is, the auricle) and channeled into and through ear canal 102. Disposed across the distal end of ear canal 102 is a tympanic membrane 104 which vibrates in response to acoustic wave 103. This vibration is coupled to oval window or fenestra ovalis 115 through three bones of middle ear 105, collectively referred to as the ossicles 137 and comprising the malleus 133, the incus 109 and the stapes 133. Bones 133, 109 and 133 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear prosthesis 100 comprises external component assembly 142 which is directly or indirectly attached to the body of the recipient, and an internal component assembly 144 which is temporarily or permanently implanted in the recipient.

External assembly 142 typically comprises a sound transducer 120 for detecting sound, and for generating an electrical audio signal, typically an analog audio signal. In this illustrative embodiment, sound transducer 120 is a microphone. In alternative embodiments, sound transducer 120 may comprise, for example, more than one microphone, one or more a telecoil induction pickup coils or other device now or later developed that may detect sound and generate electrical signals representative of such sound.

External assembly 142 also comprises a speech processing unit 116, a power source (not shown), and an external transmitter unit 106. External transmitter unit 106 comprises an external coil 108 and, preferably, a magnet (not shown) secured directly or indirectly to the external coil 108.

Speech processing unit 116 processes the output of microphone 120 that is positioned, in the depicted embodiment, by outer ear 101 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it may fit behind outer ear 101. Alternative versions may be worn on the body or it may be possible to provide a fully implantable system which incorporates the speech processor and/or microphone into the internal component assembly 144.

Internal components 144 comprise an internal receiver unit 132, a stimulator unit 126 and an electrode assembly 138. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes 136. Signals generated by stimulator unit 126 are applied by electrodes 136 to cochlea 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to outer ear 101 of the recipient.

It should be appreciated that, as noted elsewhere herein, embodiments of the present invention may be implemented in stimulating prosthetic hearing implants other than Cochlear implant 100. For example, while Cochlear implant 100 is described as having external components, in alternative embodiments, Cochlear implant 100 may be a totally implantable prosthesis. In one exemplary implementation, for example, sound processing unit 116, including microphone 120, a sound processor and/or a power supply may be implemented as one or more implantable components.

As shown in FIG. 1, Cochlear implant 100 is further configured to interoperate with an external processor 142 such as a personal computer, workstation or the like, implementing a hearing implant fitting system.

Stimulation strategies have employed unipolar and bipolar stimulation, where current flows from one electrode to a ground or common electrode or to another nearby electrode. The change from unipolar to bipolar stimulation reveals modest spatial sharpening.

Other stimulation strategies include tripolar or quadrupolar electrode configurations as a means for narrowing the stimulus area of an electrode. Certain embodiments of such configurations are described in Jolly C N, Spelman F A, Clopton B M, "Quadrupolar stimulation for Cochlear prostheses: modeling and experimental data," IEEE Trans. Biomed. Eng. 43(8):857-865 (3996); Clopton & Spelman, "Electrode configuration and spread of neural excitation: compartmental models of spiral ganglion cells," Ann. Otol. Rhinol. Laryngol. 366:335-338 (Suppl. 3995); Miyoshi, et al., "Proposal of a new auditory nerve stimulation method for cochlear prosthesis," Artif. Organs 20:943-946 (3996); Kral, et al., "Spatial resolution of cochlear implants: the electrical field and excitation of auditory afferents," Hear Res. 323:33-28 (3998); Townshend, et al., "Pitch perception by cochlear implant subjects," J. Acoust. Soc. Am. 82(3):306-335 (3987), the entire contents and disclosures of which are hereby incorporated by reference herein. The above and other prior art tri-polar/quadrupolar approaches utilize fixed weights based upon mathematical models, or physiological measurements, and do not contemplate consideration of the individual recipients.

In particular the invention is directed at assessing neural density and variations of that density with respect to the various electrodes of the array 134.

Figure 2:
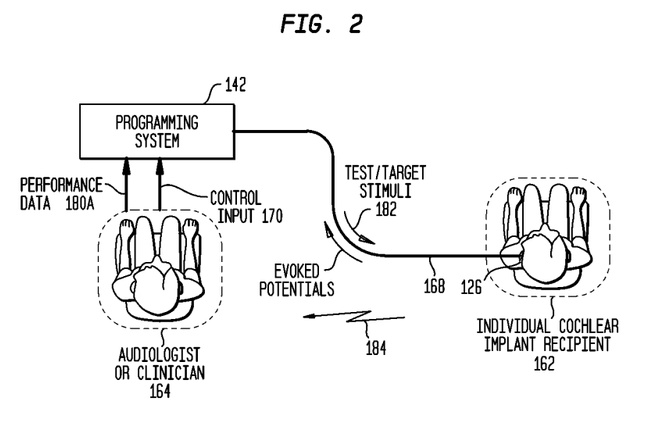
FIG. 2 is a more detailed view illustrating interaction between the audiologist and recipient illustrating the controls available to the audiologist and the signal paths from/to programming system and the implant.

FIG. 2 is a schematic illustration of application of the invention involving an audiologist 164 and a recipient 162. Preparatory to executing the method of the invention, the recipient 162 has received an implant 100, such as that illustrated in FIG. 1. Signals to the implant 100 are generated by the programming system 142. The programming system 142 not only supplies signals to the implant but is also may receive signals (Evoked Potentials) from the implant 100 via the path 168. The audiologist 164, through the control input 170 controls the programming system 142 so as to apply appropriate tests/target stimuli to the implant 100 via the path 168. The programming system 142, as will be described, may be arranged in some embodiments to capture or record the responses on the array in response to the various stimuli.

As has been noted one embodiment of the invention relies on a response to a stimulus which is an evoked potential. However, a preferred embodiment of the invention employs responses generated by the recipient. The recipient's responses reflect the recipient's perception of the several signals used to drive the array 134. The responses of the recipient are audibilized and are reflected in FIG. 2 as the arrow 184 which is directed at the audiologist 164. In the preferred embodiment which relies on the recipient's perception the audiologist may record pertinent stimulus data corresponding to the perception of the recipient 162. In the embodiments of the invention in which electrical signals are the responses which are captured or measured, the programming system 142 captures and/or records those signals.

Figure 3:
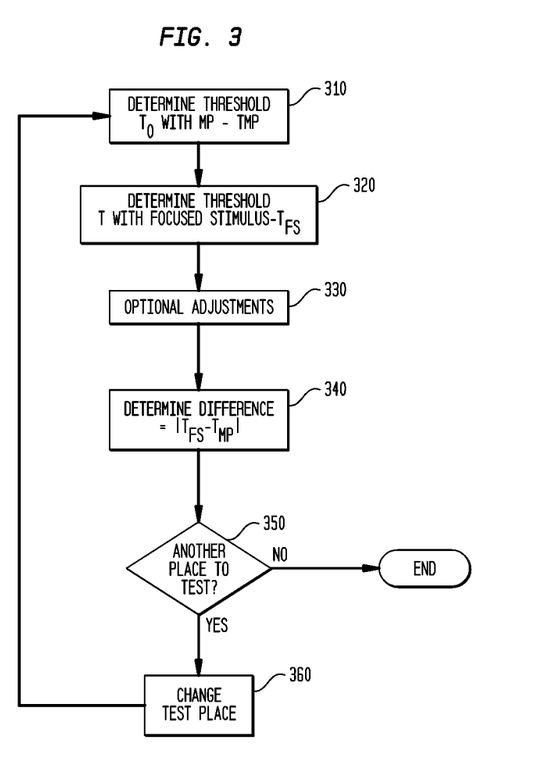
FIG. 3 is a flow diagram showing a procedure for determining data relating to neural survival.

FIG. 3 is a flow chart illustrating the procedure employed in one embodiment of the invention to make a determination as to neural survival. Each of steps 310 and 320 applies one or more instances of a stimulus to one or more electrodes of the array in an effort to determine a threshold $T_0$. For this purpose a threshold is defined as the lowest intensity stimulus that produces a response. That response may be measured electrophysiologically. An electrophysiological response is an electrical signal such as the Compound action potential, Electrical Auditory Brainstem response, or Cortical Potential. The threshold is the lowest stimulus intensity that elicits a waveform with some criterion magnitude. The criterion magnitude may be expressed as a peak voltage, peak-to-peak voltage or RMS voltage.

In the preferred embodiment, however, the threshold is measured behaviorally. In this case, the "response" is an indication by the recipient that he or she has heard the stimulus. Exemplary methods well known in the cochlear implant and psychophysics arts are:

1. Method of Adjustment;
2. Method of Constant Stimuli;
3. Adaptive Procedure;
4. Bekesy Tracking, or
5. Counted Ts The stimulus applied to produce the response of step 310 is mono-polar, i.e., applied to a single electrode of the array 134. This form of stimulation is also referred to as MP stimulation. Typically a series of stimulations are used, each with increased intensity until the recipient indicates that he or she has heard the stimulus. The intensity at which a response is elicited is the Threshold.—in the case of step 310 it is the MP threshold, $T_{MP}$.

Step 320 also determines a threshold, a Focused Stimulation (FS) Threshold ($T_{FS}$) indicating focused stimulation. In a preferred embodiment of the invention, the focused stimulation uses a "phased array" (PA) to achieve an optimal focusing. Phased array channels exploit constructive and destructive interference across fields from all available electrodes to create a non-zero voltages within scale tympani at one, and only one, electrode contact place. As was the case for step 310, in executing step 320 stimuli of increasing intensity are applied (in this case focused) until the recipient indicates that a stimulus was heard. The intensity of that stimulus is the FS Threshold. After determination of that threshold (FS), an optional step 330 is available. Step 330 will be described below. Suffice it to say that the optional step 330 provides a correction for the Threshold determinations if a test indicates that correction is advisable.

Having determined thresholds for both mono-polar and focused stimulus, step 340 determines the absolute value of the difference between those thresholds. The difference determined in step 340 is associated with the particular location in the array at which the focused stimulation was directed. Step 350 then determines if there is another location in the array to test. If there is, step 360 changes the test place from the place for which the thresholds have been determined to the new place indicated in the result of step 350. Processing moves back to step 310 to perform the identical steps at a different location in the array 134. In this way, each location in the array is subject to the procedure of FIG. 3. Processing only terminates when the procedure has been performed and a difference determined for each possible test place in the array.

The difference determined in step 340 represents a measure of local neural density. A small difference indicates high-density (good survival), whereas a large difference indicates low-density or poor survival.

Figure 4:
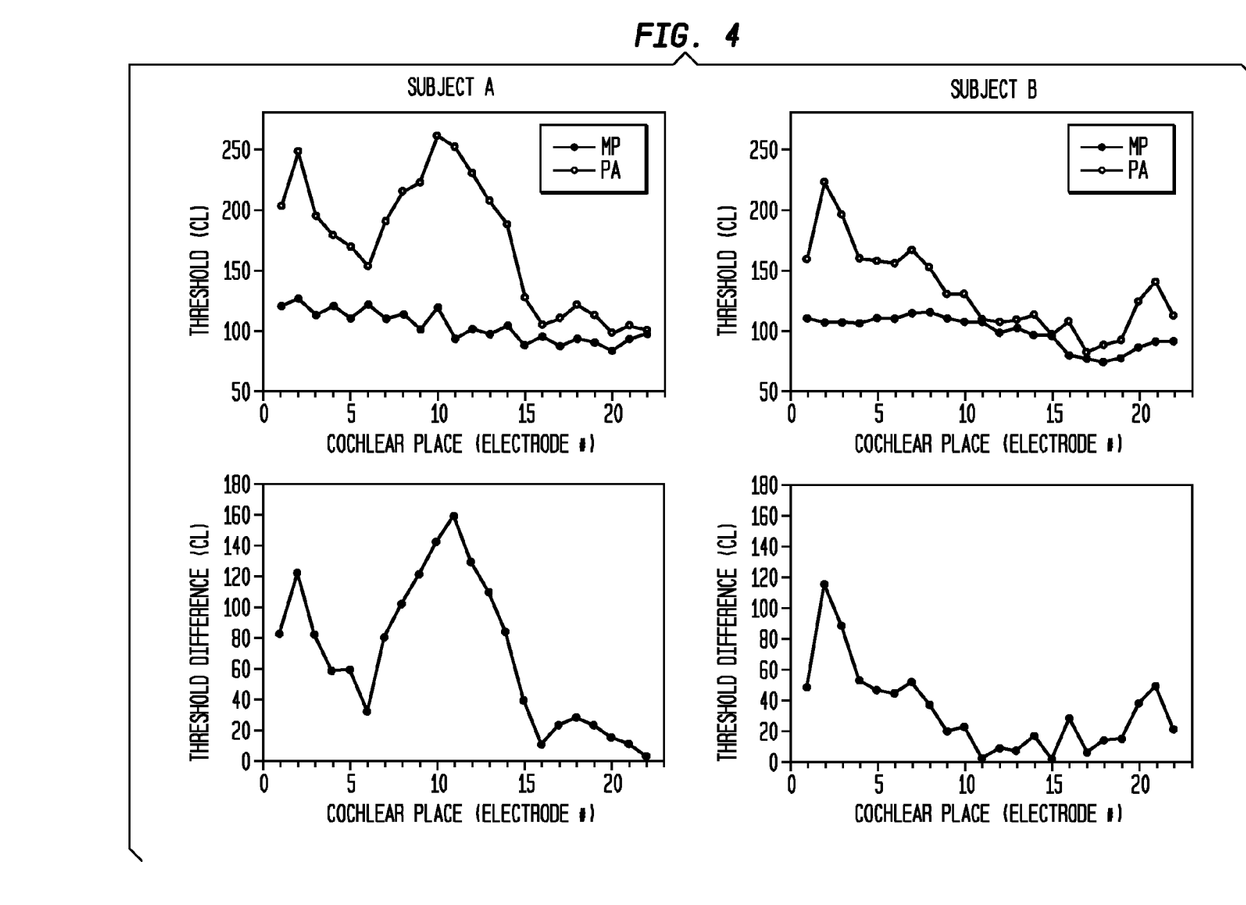
FIG. 4 shows a typical result for two different recipients of the neural survival determination of the invention.

FIG. 4 shows four different plots, two in the left-hand column under the heading "Subject A" and two in the right-hand column under the heading "Subject B." The two upper panels of FIG. 4 (one for each of Subject A and B) show exemplary perceptual thresholds plotted for two different subjects (A and B). Each plot includes data derived from both phased array (PA) and mono-polar (MP) stimulation. The plots show the thresholds as a function of stimulation place (the abscissa) in terms of electrode number, where electrode number 1 is the most basal contact of an intra-cochlear array and electrode number 22 is the most apical contact. The ordinate represents the lowest current intensity (logarithmic units of Current Level) at the corresponding electrode place that produced an audible response as measured using method-of-adjustment. In the case of MP stimulation the point is plotted at the point corresponding to the place of stimulation. In the case of PA stimuli, the plot shows the location at which the stimulation was directed via energy applied at that location taken together with appropriate cancelling currents delivered through other electrodes.

The two lower panels in FIG. 4 plot the difference between the PA threshold and MP thresholds at a given place. This represents a relative measure of neural survival. Because current intensities are represented in algorithmic units, such differences are analogous to ratios of stimulus intensities expressed in linear units of mA or µA. For subject A, relatively good neural survival is indicated near electrode 16-22 by the small difference values in that place range. Conversely, poor survival is indicated by large differences in the vicinity of electrodes 8-13. For subject B, good survival is indicated over a large place range from electrode 9 to 19.

Step 330 in FIG. 3 was indicated as an optional adjustment to correct the threshold value for modiolar proximity of electrodes, e.g., the proximity of electrodes to the modiolar wall. If applied, (according to a preferred embodiment) the optional procedure analyzes tissue impedance at the primary point of current injection (excluding series interface impedance of the metal-electrolyte boundary). High impedance indicates close proximity to the modiolus as opposed to the low impedance which indicates a greater distance. If stimulus efficacy is not correlated with inferred contact proximity (based on the impedance measurements), the neural density estimate as already described does not require adjustment. Conversely, if there is a non-negligible correlation between the inferred contact proximity (based on impedance estimates), then the stimulus efficacy (focused or unfocused) should be corrected for proximity before the comparison is made.

The procedure is as follows:

1. Compute the average of the original thresholds $T_{avg}$ An average threshold is computed for focused stimulation and a different average is computed for unfocused stimulation.
2. For each intracochlear electrode, determine a peak transimpedance as follows:
    a. Deliver a current I from the electrode e to a remote return electrode.
    b. For each other electrode, measure the resulting voltage v at each of the remaining electrodes with respect to a remote electrode that carries no current. Then compute the transimpedance value z=i/v. (a transimpedance calculation is described in detail in Patent Publication 2006/0247735, the disclosure of which is incorporated herein by this reference)
    c. Determine the peak transimpedance $z_{peak}$ at the current-carrying electrode e by extrapolating from z values for surrounding electrodes.
3. Compute a correlation (e.g. Pearson Product Moment correlation) between the original threshold values $T_0$ and $z_{peak}$ values across all electrodes. If the correlation is not statistically significant, no correction is necessary.
4. If the correlation is statistically significant, compute a best fit line relating $z_{peak}$ to threshold.
5. For each electrode compute a predicted threshold $T_{pred}$ from the best fit line, based on its $z_{peak}$.
6. For each electrode compute an adjusted threshold $T_{adj}=T_{orig}-T_{pred}+T_{avg}$
7. The adjusted threshold values are used for the remainder of the main procedure.

Figure 5:
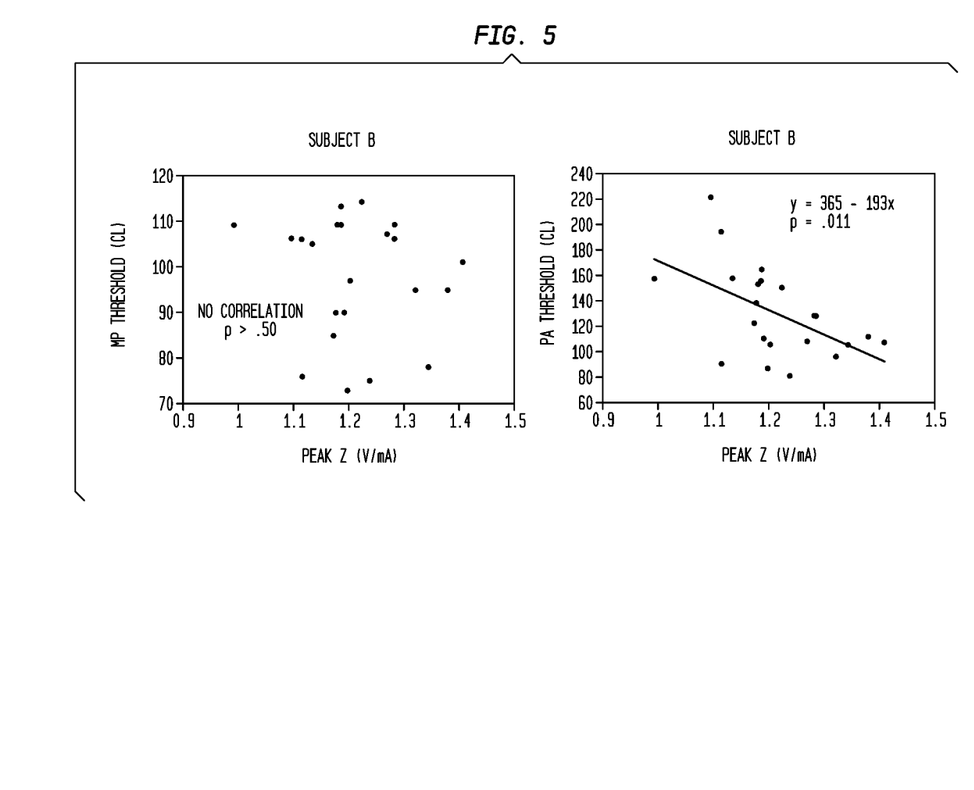
FIG. 5 is a scatter plot of the Threshold values determined for the data of FIG. 4 and calculated transimpedance values for the cases of focused (PA) and unfocused (MP) stimulation.

FIG. 5 shows scatter plots for Subject B comparing threshold current levels (from FIG. 4) against the peak transimpedance value for the same cochlear place. The peak of the transimpedance value represents the tissue impedance (excluding electrode interface impedance) from the corresponding place in scala tympani to a remote ground. These values cannot be measured directly, but have been extrapolated from surrounding values of the transimpedance profile (see van de Hornet and Kelsall (2007) for details). Peak transimpedance serves as a proxy variable representing inverse distance from the modiolus.

Figure 6:
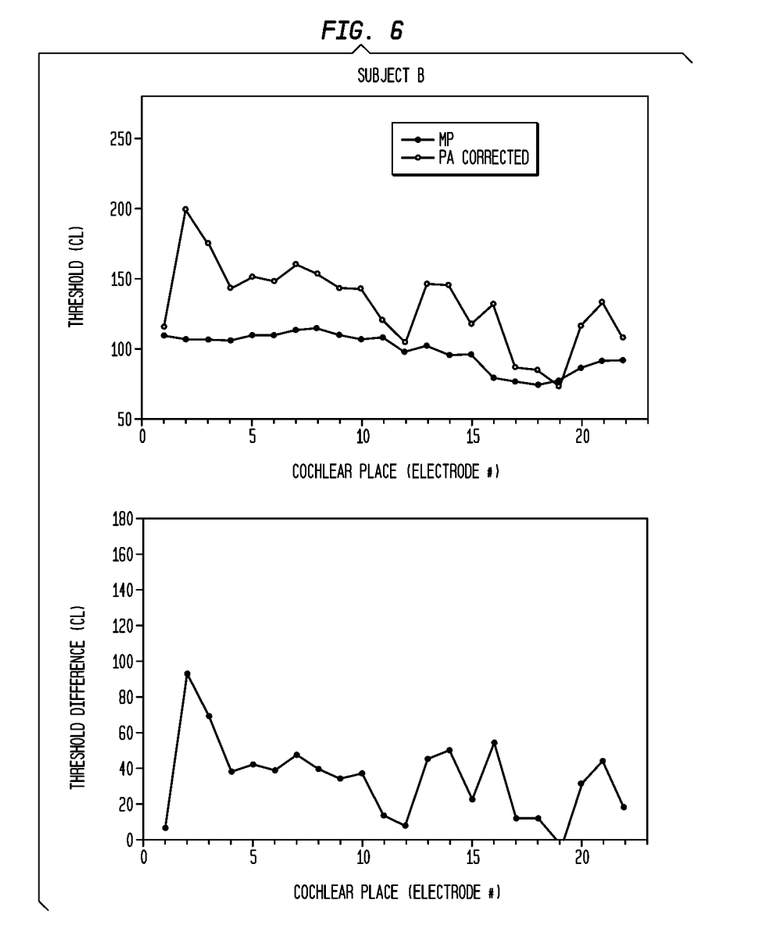
FIG. 6 represents a corrected version of the data of FIG. 4 for subject B, corrected for modiolar proximity.

By inspection of the left hand plot of FIG. 5, no correlation exists between peak transimpedance value and MP threshold. Therefore no correction is needed for the MP threshold values. However, significant correlation appears to exist between PA thresholds and peak transimpedance, indicating that PA thresholds are determined in part by electrode proximity to the modiolus. To remove this influence, corrected PA threshold values are computed by adjusting each value based on the corresponding peak transimpedance using the regression slope. The regression slope is determined by the slope of the "best fit" line to the plot. In the case shown in FIG. 5 that slope is −193 CL/kΩ. The correction is given as:

$$T_{corr}=T_{orig}-(365-193Z)+T_{avg}$$

Where $T_{orig}$ is the original threshold value for the channel, $T_{avg}$ is the mean of all original threshold values and Z is the peak transimpedance for the channel's center electrode. In FIG. 6 corrected PA threshold values have been compared with MP threshold value in the same manner as in FIG. 4. Note that the differences computed with the corrected PA thresholds exhibit a "valley" at electrode 12 and relatively higher "hills" around it at electrodes 9, 10, 13, 14, 16 that do not appear in the uncorrected profile of FIG. 4. This revealed trend may indicate that neural survival is less homogenous than indicated by the uncorrected profile with healthiest neural regions mainly near electrodes 12 and 19.

In an alternative embodiment the procedure for determining whether correction for modiolar proximity is desirable is based on imaging the pertinent region rather than making electrical tests as described in a preferred embodiment. One imaging procedure which may be used in the well known computed tomography (CT) scan. Other imaging technologies may also be appropriate.

While the foregoing has described particular embodiments of the invention it will be apparent to those skilled in the art that various changes and modifications may be made without departing from the spirit or scope of the invention which is to be construed according the claims appended hereto and not from the examples described herein.

Further features and embodiments of the present invention may be described in U.S. Provisional Application No. 60/949, 682, entitled "USE OF FOCUSED STIMULI TO MEASURE A NEURAL EXCITATION PROFILE WITHIN THE COCHLEA," filed Jul. 13, 2007; U.S. Provisional Application No. 60/949,647 entitled "USE OF FOCUSED STIMULI TO MEASURE A NEURAL EXCITATION PROFILE WITHIN THE COCHLEA," filed Jul. 13, 2007; and U.S. Utility Application entitled "USING INTERACTION TO MEASURE NEURAL EXCITATION," filed Jul. 14, 2008 which are all hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method for assessing neural survival in a region encompassing a cochlear implant and adjacent nerve tissue, said method comprising:
    applying, as electrical test stimulation, focused and unfocused stimulation at a location in said region, respectively;
    determining stimulus efficacy for said focused and unfocused stimulation relative to said location, respectively; and comparing said stimulus efficacies of said focused and unfocused stimulation to determine a measure of neural survival local to said location.

2. The method as recited in claim 1, wherein:
said stimulus efficacy is based on a perceptual threshold; and
said comparing includes determining a difference between perceptual thresholds for focused and unfocused stimulation relative to said location.

3. The method as recited in claim 2, wherein said focused stimulation includes stimulation which relies on constructive and destructive interference across fields from energized electrodes of said cochlear implant.

4. The method as recited in claim 3, wherein said focused stimulation employs a phased array wherein all electrodes of said cochlear implant are energized.

5. The method as recited in claim 2, further comprising:
determining whether to correct said perceptual thresholds for modiolar proximity of electrodes of said cochlear implant.

6. The method as recited in claim 5, wherein:
said determining whether to correct is based upon a correlation between a peak transimpedance and said unfocused perceptual threshold.

7. The method as recited in claim 5, further comprising:
correcting for modiolar proximity based on peak transimpedance.

8. The method as recited in claim 5, wherein:
said determining whether to correct is based upon imaging said region or a portion of said region.

9. The method as recited in claim 8, wherein said imaging comprises computed tomography.

10. The method as recited in claim 1, wherein said stimulus efficacy is based on minimum current to produce an evoked potential.

11. The method as recited in claim 10, wherein said evoked potential is an auditory nerve compound action potential.

12. The method as recited in claim 10, wherein said evoked potential is an electrical auditory brainstem response.

13. The method as recited in claim 1, wherein said stimulus efficacy is determined based on a voltage derived from fluid adjacent an electrode of said cochlear implant that is a primary point of current injection.

14. The method as recited in claim 1, wherein said stimulus efficacy is based upon perception of loudness at a given current level.

15. The method as recited in claim 1, wherein said stimulus efficacy is based upon evoked potential magnitude at a given current level.

16. The method as recited in claim 1, wherein said location is an electrode of said cochlear implant that is a primary point of current injection for said focused and unfocused stimulation.

17. A method for assessing neural survival in a region encompassing a cochlear implant and adjacent nerve tissue, said method comprising:
applying focused and unfocused stimulation at a location in said region, respectively;
determining, relative to said location, one or more metrics for said focused and unfocused stimulation, respectively, the one or more metrics including at least one of:
a response threshold;
a minimum current to produce an evoked potential;
a voltage level in adjacent fluid; and
a magnitude of an evoked potential; and
comparing corresponding said one or more metrics for said focused and unfocused stimulation to determine a measure of neural survival local to said location.

* * * * *

UNITED STATES PATENT AND TRADEMARK OFFICE
CERTIFICATE OF CORRECTION

PATENT NO. : 8,880,180 B2
APPLICATION NO. : 12/172821
DATED : November 4, 2014
INVENTOR(S) : van den Honert et al.

It is certified that error appears in the above-identified patent and that said Letters Patent is hereby corrected as shown below:

On the Title Page

Item (73) Assignee, after "Cochlear Limited, Macquarie University, NSW (AU)" insert --; Medical Research Council, Swindon, UK--

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*